United States Patent
Leko

(10) Patent No.: US 6,576,270 B2
(45) Date of Patent: Jun. 10, 2003

(54) HERBAL COMPOSITION AND MEDICAMENT AGAINST DIABETES MELLITUS TYPE II MANUFACTURED THEREOF

(76) Inventor: Vladimir Leko, Josipa Kozarca 4, 34310 Pleternica (HR)

( * ) Notice: Subject to any disclaimer, the term of this patent is extended or adjusted under 35 U.S.C. 154(b) by 0 days.

(21) Appl. No.: 09/952,055

(22) Filed: Sep. 11, 2001

(65) Prior Publication Data

US 2002/0102315 A1 Aug. 1, 2002

Related U.S. Application Data

(63) Continuation of application No. PCT/HR99/00008, filed on Apr. 22, 1999.

(30) Foreign Application Priority Data

Mar. 12, 1999 (HR) .......................................... P990080A

(51) Int. Cl.$^7$ ........................ A61K 35/78; A61K 47/00; A61K 9/20; A61K 9/66
(52) U.S. Cl. ....................... 424/733; 424/733; 424/757; 424/773; 424/774; 424/777; 424/778; 424/439; 424/464; 424/745; 424/455; 424/725; 514/783; 514/866
(58) Field of Search ................................. 424/725, 733, 424/757, 773, 774, 777, 778, 439, 464, 745, 455; 514/783, 866

(56) References Cited

U.S. PATENT DOCUMENTS 5,922,769 A * 7/1999 Barelli et al.

* cited by examiner

Primary Examiner—Christopher R. Tate
Assistant Examiner—Michele C. Flood
(74) Attorney, Agent, or Firm—St. Onge Steward Johnston & Reens LLC

(57) ABSTRACT

The invention relates to the herbal composition which consists of: *Centaurii umbellatum,* Gentianaceae (centaury plant), *Teraxacum officinale,* Asteraceae (dandelion root), *Juniperi communis* L, Cupresaceae (juniper berry), *Urticae dioica* L, Urticeae (nettle plant), *Urticae dioica* L, Urticaceae (nettle root), *Cichorium intybus* L, Cichoriaceae (chicory root), *Morus nigra* L, Moraceae, (mulberry leaf), *Achilleae millefolium* L, Asteraceae (yarrow flower), *Vaccinium myrtillus* L, Ericaceae (bilberry leaf), *Phaseolus vulgaris* L, Fabaceae (bean pods), *Valeriana officinalis* L, Valerlanaceae (Valerian root).

8 Claims, 3 Drawing Sheets

HERBAL COMPOSITION AND MEDICAMENT AGAINST DIABETES MELLITUS TYPE II MANUFACTURED THEREOF

The present application is a continuation of pending International Patent Application PCT/HR99/00008 filed Apr. 22, 1999, which designates the United States, and which claims priority of Croatian patent application P990080A filed Mar. 12, 1999.

FIELD WHICH THE INVENTION REFERS TO

This invention refers to the field of pharmacy, and more closely, it refers to the medicament against diabetes mellitus type II, and even more precisely, it refers to the medicament against diabetes mellitus type based on a herbal composition as an active substance. According to the International Classification of Patents, the subject invention is marked with the classification symbol A 61 K 35/78—Medical preparations containing substances or products of their reactions with undefined composition, whereby substances from herbs are in question.

1. Technical Problem

The technical problem, the solution of which is disclosed in this patent application, consists in finding a medicament for diabetes mellitus type II which will have the following characteristics: 1) that it is suitable for peroral application; 2) that even very high values of glucose concentration in blood can be reduced to or near its normal value; 3) no evident harmful side effects occur even in case of large daily doses, and even in case of a long-time use; and 4) that its effectivess is not caused by a strict diet.

2. State of the Art

Insulin, a hormone produced by the pancreas, makes glucose available to cells in the human body for the purpose of obtaining energy. In case of diabetes mellitus type I the pancreas produces little insulin or it does not produce it at all and insulin must be injected daily so that a diabetic would survive. With diabetes mellitus type II the pancreas produces insulin, but the quantity of insulin is insufficient or it is less effective due to the cellular resistence, or both. In each of these forms there are various abnormalities, but the basic defects to which these abnormalities can be attributed are: 1) the reduced entering of glucose into various "peripheral" tissues; and 2) the increased releasing of glucose from the liver into the bloodstream (increased liver glucogenesis). Therefore, there is an extracellular surplus of glucose and an intracellular lack of glucose, which can be called "starving amidst abundance".

For treatment of diabetes mellitus type II, there are many peroral hypoglycemic remedies, generally from the class of sulphonylureas, and from the group of biguanides. The class of sulphonylureas includes, e.g. chlorpropamide (the trade name: Meldijan, etc.), carbutamide (some 40 trade names), glybenchlamide (trade names: Euglukon, Glibenklamid Genericon, etc.), etc., while the group of biguanides includes, e.g. phenyl-ethyl-biguanide (trade names: Phenformin, DB-Comb, etc.), dimethyl-biguanide (trade names: Gluchopage, etc.), etc.

The main shortcomings of the stated groups of medicaments lie in: numerous harmful side effects, numerous counterindications (e.g. impossibility of application in pregnancy and during the suckling period), frequent impossibility of reducing a very high value of the concentration of glucose in blood to the normal value or very close to it, and the fact that the effectiveness of the medicament by strict observing of a diet.

DESCRIPTION OF THE INVENTION

Figure 1:
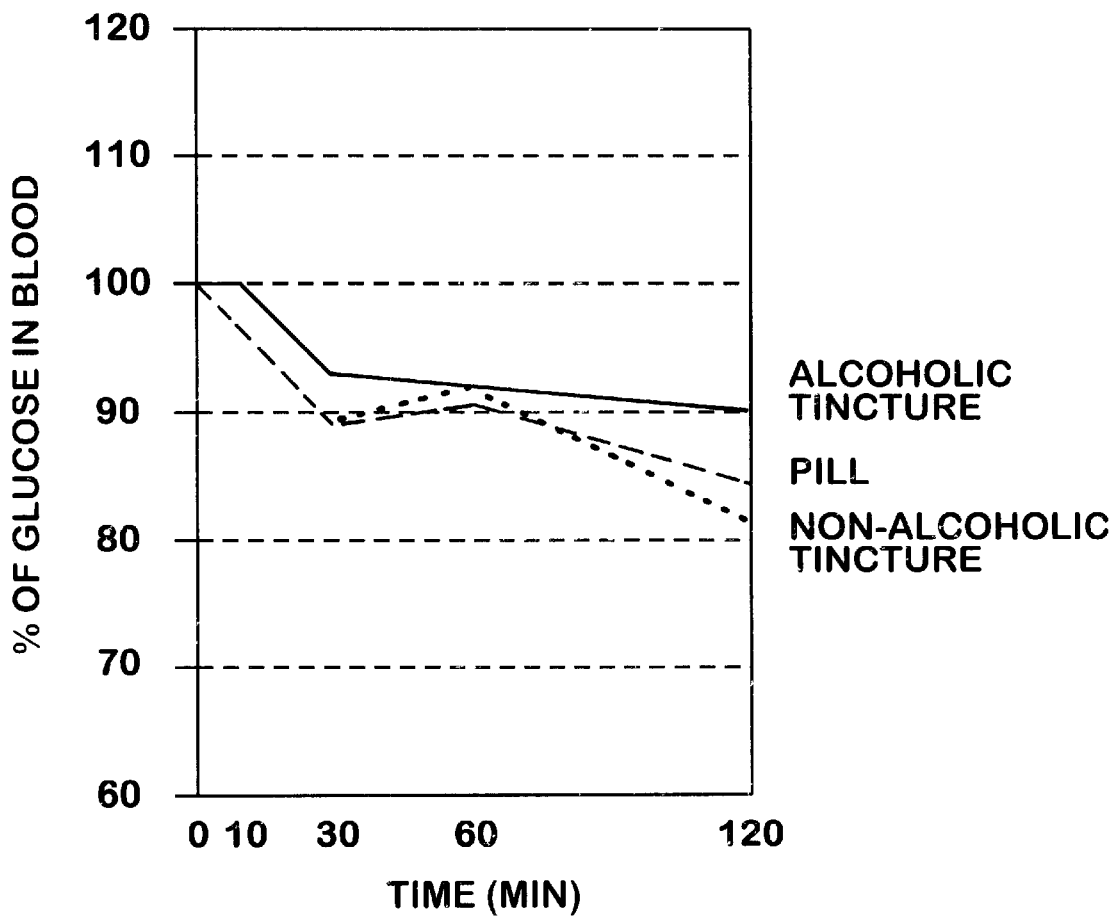
FIG. 1. is a graph showing decreasing glucose concentration in CBA diabetic mice after taking herbal preparation.

The inventor approached the solving of the technical problem set forth in this Application for Patent starting with the viewpoint that in case of diabetes mellitus type II an illness of disturbed metabolism is actually in question, and that for a successful treatment of diabetes mellitus type II it is not sufficient to use a medicament which has only the characteristic of strong hypoglycemism, but that a medicament which will help the disturbed metabolism in its entirety should be used here. Moreover, having in mind the enormous influence of psyche on the body (e.g. stress increases the load on beta cells of the pancreas), as one condition, the inventor made a request on the required medicament that it should contain at least one component which has a soothing effect on psyche.

Through many previous testing carried out in respect of determining the most suitable contents of the herbal composition which would be used as the starting substance for obtaining a medicament for oral application, in form of tea and in form of a herbal tincture , the inventor ascertained that favourable results are achieved with a herbal composition made from the following dried ingredients: the plant of centaury (*Centaurii herba*), the root of dandelion (*Teraxaci radix*), the fruit of juniper (*Juniperi communis fructus*), the plant of nettle (*Urticae herba*), the root of nettle (*Urticae radix*), the root of chicory (*Cichorii radix*), the leaf of black mulberry (*Morus nigra folium*), the flower of yarrow (*Achilleae millefolii flos*), the leaf of bilberry (*Vaccinii myrtilli folium*), the pod of beans (*Phaseoli fructus sine semeni*) and the root of valerian (*Valerianae officinalis radix*).

Although the application of numerous plants was described in corresponding fields, the synergic combination according to this invention has never been disclosed before.

Testings on volunteers and rodents proved that positive results in treatment were achieved if the medicament, made in the form of a tea, a herbal tincture and a pill, was obtained from the herbal composition with its percentage shares lying in the intervals shown in Table 1.

TABLE 1

| | |
|---|---|
| the plant of centaury (*Centaurii herba*) | 10–15% by wt. |
| the root of dandelion (*Teraxaci radix*) | 6–12% by wt. |
| the fruit of juniper (*Juniperi communis fructus*) | 5–8% by wt. |
| the plant of nettle (*Urticae herba*) | 5–10% by wt. |
| the root of nettle (*Urticae radix*) | 5–10% by wt. |
| the root of chicory (*Cichorii radix*) | 12–20% by wt. |
| the leaf of black mulberry (*Morus nigra folium*) | 5–10% by wt. |
| the flower of yarrow (*Achilleae millefolii flos*) | 2–5% by wt. |
| the leaf of bilberry (*Vaccinii myrtilli folium*) | 4–10% by wt. |
| the pod of beans (*Phaseoli fructus sine semeni*) | 10–20% by wt. |
| the root of valerian (*Valerianae officinalis radix*) | 5–10% by wt. |

However, by far the best results in treatment of diabetes mellitus type II were obtained by administration of a tea, a herbal tincture and a pill obtained from the herbal composition with its percentage shares shown in Table 2.

TABLE 2

| | |
|---|---|
| the plant of centaury (*Centaurii herba*) | 12.3% by wt. |
| the root of dandelion (*Teraxaci radix*) | 9.7% by wt. |
| the fruit of juniper (*Juniperi communis fructus*) | 6.2% by wt. |
| the plant of nettle (*Urticae herba*) | 7.4% by wt. |
| the root of nettle (*Urticae radix*) | 7.0% by wt. |
| the root of chicory (*Cichorii radix*) | 17.7% by wt. |
| the leaf of black mulberry (*Morus nigra folium*) | 7.4% by wt. |
| the flower of yarrow (*Achilleae millefolii flos*) | 3.5% by wt. |
| the leaf of bilberry (*Vaccinii myrtilli folium*) | 6.6% by wt. |
| the pod of beans (*Phaseoli fructus sine semeni*) | 14.4% by wt. |
| the root of valerian (*Valerianae officinalis radix*) | 7.8% by wt. |

Now follows a short presentation of the ingredients listed above, by their contents and effect, as they are described in the known literature.

1. *Centaurii herba*

*Centarium umbellaturm,* Gentianaceae—centaury

SPREAD: Europe, North America, North Africa and western part of Asia. It is imported from Bulgaria, Hungary, Croatia, Bosnia and Herzegovina, Macedonia.

CURATIVE PART OF THE PLANT: part above the earth.

TIME OF BLOOMING: June-September

TIME AND WAY OF COLLECTING: it is picked during blossoming and dried in the air.

ACTIVE SUBSTANCES: small quantity of bitter substances (centapicrine, svertiamarine, sveroside and gentiopicroside). The drug contains up to 0.4% of flavonoid, methoxylized xanthone derivatives: methyl-belidifolin, phenol-carboxylic acid, triterpenes, triterpenes, sterols. 2-hydroxy- and 2.5-dihydroxy-terephthalic acid are present in surrounding parts and the root.

INDICATIONS: due to bitter substances, it is used to stimulate the appetite and the secretion of the gastric juices (particularly in chronical dyspeptic conditions and acheilia).

In popular medicine it is also used as a roborant and a tonic.

2. *Teraxaci radix*

*Taraxacum officinale,* Asteraceae—dandelion

SPREAD: a plant growing wild across the northern hemisphere, with many different kinds; it is collected wild and cultivated, mostly in countries of Eastern Europe.

CURATIVE PART OF THE PLANT: part above the earth and root.

TIME OF BLOOMING: March-May.

TIME AND WAY OF COLLECTING: it is picked in April and May. It is dried in the air or at an artificial temperature of 40° C.

ACTIVE SUBSTANCES: bitter substances called taraxacyne: tetrahydroridentin B and taraxacolide β-D-glucopyranoside, and similar new germakranolides (taraxic β-D-glucopyranoside and 11,13-dihydrotaraxine acid of β-D-glucopyranoside, triterpenes (taraxasterol, α-taraxasterol, their acetates and 16-hydroxy-derivates arnidol and faradiol), sterols (sitosterol, stigmasterol), carotenoids (xanthophyls), flavonides (apygenin), carbohydrates (in the root, containing about 1% of slime). In spring, the drug contains 18% of sugar (fructose), and 2% of inulin, which by autumn reaches even up to 40%.

INDICATIONS: mild choleretic, diuretic, appetite stimulant (bitter substances), as adjuvant in case of liver disturbances and troubles with gall-bladder, and in case of digestive disturbances (particularly in case of incomplete digestion of fat).

In popular medicine it is used for "cleansing of blood", then, as mild laxative, in case of arthritis and rheumatic troubles, rash and other skin problems. Except for tea, it is used as juice obtained by pressing fresh plants. In spring, it is favourable for salade, and in autumn the root can be used as a replacement for coffee (due to large quantities of insulin).

Diuretic and saluretic effect of the fluid tincture was recently proved on rats. The effect was similar to the effect of furosemides, and stronger than other vegetable diuretics (*Equiseti herba, Juniperi fructus*) and that without toxic side effects.

3. *Juniperi fructus*

*Juniperi communes* L, Cupresaceae—juniper

SPREAD: a plant growing wild in Europe, North America and northern parts of Asia. It is imported from Italy, Croatia, Bosnia and Herzegovina, Macedonia, Albania.

CURATIVE PART OF THE PLANT: berries, and etherical oil obtained from them.

TIME OF BLOOMING: April, May.

TIME AND WAY OF COLLECTING: in October, only ripe berries are collected and dried in the air.

ACTIVE SUBSTANCES: 0.5–2.0% of etherical oil, with over seventy isolated ingredients: the main component are monoterpenes: α- and β-pinene (16.5–80%), sabinene (0.2–50%), limonene (1–12%), terpinene-4-ol, borneol, geraniol, α-terpineol. Sesquiterpenes, phenols and ethers are present in traces.

INDICATIONS: diuretic and uroantiseptic. As diuretic agent, it can lead to the irritaion of kidneys (sometimes, toxicity as well), so that is the reason why it is not in pharmacopeia. The stated unwanted effects are mostly due to terpenes (pinene).

In popular medicine it is used as stomachic, carminative, and aromatic in case of dyspeptic disturbances (and that indication was the only one stated in pharmacopeia).

COUNTERINDICATIONS: pregnancy and inflammatory kidney processes.

4. *Urticae herba*

5. *Urticae radix Urtica dioica* L, Urticaceae—nettle

SPREAD: growing wild throughout the world; mostly Central and Eastern Europe.

CURATIVE PART OF THE PLANT: part above the earth and root.

TIME OF BLOOMING: May-September.

TIME AND WAY OF COLLECTING: leaves are collected from May to August and dried in the air.

ACTIVE SUBSTANCES: flavonoides (glycosides of quercetin, rhametin in flowers), chlorophyl A and B, caretonides (including β-carotene and xanthophyl), vitamins (group B and C, and vitamin K1), triterpenes and sterols (including β-sterol), mineral salts (nitrates, potassium salts) and acids: formic acid, acetic acid, citric acid, etc.

INDICATIONS: diuretic. Two weeks treatment increases the volume of urine and reduces the body weight.

In popular medicine the greenness of the nettle prepared as tea or juice (by pressing of the fresh plant) is used in many ways: internally as a diuretic, in case of rheumatism and arthritis, as a component of "antidiabetic" tea, for quicker healing of wounds. Externally in case of seborrhea and against the loss of hair.

6. *Cichorii herba*

*Cichorium intybus* L, Cichoriaceae—chicory, succory

SPREAD: as autochtonic kind only in Europe, Northern America and part of Asia. During the century it spread to almost all the continents.

CURATIVE PART OF THE PLANT: part above the earth and root.

TIME OF BLOOMING: June-September.

TIME AND WAY OF COLLECTING: the plant is collected in the beginning of summer and dried in the air, and the root is dug out in late autumn, it is to be well washed, cut longitudinally and dried in the airy and dry place.

ACTIVE SUBSTANCES, the root contains inulin, free fructose, glycoside intubin, tannin. The stalk and flowers contain glycoside chicorin.

INDICATIONS: choleretic, diuretic, for improving of appetite.

7. *Mori folium*

Morus nigra L, Moraceae—black mulberry

SPREAD: south-eastern Europe and Asia.

CURATIVE PART OF THE PLANT: fruit, leaf.

TIME AND WAY OF COLLECTING: young leaves, April-May.

ACTIVE SUBSTANCES: calcium carbonate, asparaginic acid, adeninde, glucose, peptone.

8. *Millefoli herba*

Achillea millefolium L, Asteraceae—yarrow

SPREAD: Europe, Northern America and Northern Asia. Main croppers are countries of eastern and south-eastern Europe.

CURATIVE PART OF THE PLANT: blooming plant (without the root).

TIME OF BLOOMING: June-October.

TIME AND WAY OF COLLECTING: during the blossoming, blooming plants are collected and dried in bundles. Thickened parts are removed.

ACTIVE SUBSTANCES: 0.2–1% of etheric oil which can, but need not contain kamasulen (depending on the number of chromosomes—only tetraploid plants contain kamasulen, and most of other karyotypes do not).

In plants which do not contain kamasulen, the content of the etherical oil is the following: monoterpenes (linalool), sesquiterpenes, camphor (18%), sabinene (12%), 1.8-cineole (10%), isoartemisia-ketone (9%) and α-pinene (9%).

Etherical oil which contains kamasulen has the following contents: monoterpenes, sesquiterpenes, kamasuien (25%), β-pinene (23%), caryophyllen (10%) and α-pinene (5%). As one of the proasulenes was identified achillicine (8acetoxy-artabsine).

Other present substances: guaianolides 2,3-dehydrodesacetoxy- and 8-desacetyl-matricine and leucodine, 3-oxaguaianolides 8-acetyl- and 8-angeloilegelolid, germakranolides milefine, dihydroparthenolides, balhanolid-acetate, etc., flavonoids apygenin and glycosil-flavones (svertizin, vicenin-2 and -3), phenolic acid, triterpenes and sterols, cis- and trans-matricaria ester.

INDICATIONS: mostly because of kamasulen and flavonoids, it is used as antiflogistic, spasmolytic, carminative and collagogum. The main application is in case of gastrointestinal disturbances (diarrhea, flatulence, cramps). It is used for improving appetite, and for stimulation of the secretion of bile—choleretic effect was confirmed by trials on animals.

In case of inflammatory skin processes and for quicker healing of wounds, it is used in form of a lotion, baths, and, mostly, alcoholic preparations (percolates, fluid tinctures). Water and ether tinctures have an antibacterial effect.

In popular medicine it is used as chemostyptic—in case of hemorrhage due to hemorrhoids, menstrual disturbances.

9. *Myrtilli folium*

Vaccinium myrtillus L, Ericaceae—billberry

SPREAD: North and Central Europe. It is also exported from south-eastern part of Europe (Croatia, Bosnia and Herzegovina, Macedonia, Albania, Poland).

CURATIVE PART OF THE PLANT: fruits and leaves.

TIME OF BLOOMING: May, June.

TIME AND WAY OF COLLECTING: fruits are picked when they are completely ripe, they are dried in the air (the temperature should not exceed 40–50° C.). Leaves are collected young and dried in the shadow.

ACTIVE SUBSTANCES: catecholic tannins (0.8–6.7%), leucoanthocyanides, flavonoids (mostly glycosides of quercetin), phenol-carboxylic acids, iridoides. The presence of chrome, alkaloids mirtin and epimirtin was noticed, while arbutin and hydrokinin are found only in traces.

INDICATIONS: externally as an adstringent.

In popular medicine it is used for regulation of an increased level of blood sugar and it is frequently found within "antidiabetic" teas. This effect is mostly attributed to chrome which is part of the so-called glucoseolerating factor, and mentioned as a possible effect of flavonoids. Researches are still under way.

10. *Phaseoli pericarpium*

Phaseolus vulgaris L, Fabaceae—beans

SPREAD: cultivated plant of European countries (Bulgaria, Hungary, Croatia, Macedonia).

CURATIVE PART OF THE PLANT: the pod (shell) without seeds.

TIME OF BLOOMING: June-September.

TIME AND WAY OF COLLECTING: completely ripe pods are collected. Seeds are removed, and the pod is dried in the sun.

ACTIVE SUBSTANCES: albumins, carbohydrates, various amino acids, chrome salts, silicic acids.

INDICATIONS: only in popular medicine as diuretic and mild antidiabetic. Until recently, it was believed that arginine and silicic acid are responsible for antidiabetic effect, but the latest researches ascribe it to chrome salts (endeavours are made to prove the effectiveness in diabetes mellitus type II).

11. *Valerianae radix*

Valeriana officinalis L, Valerianaceae—valerian, aliheal

SPREAD: growing wild in Europe and Asia, cultivated in Netherlands, Belgium, France, eastern Europe, Japan and USA.

HEALING PART OF THE PLANT: roots.

TIME OF BLOOMING: May-September.

TIME AND WAY OF COLLECTING: roots are dug out in September. It is to be cleaned, washed and side roots are to be removed. It is to be dried in the air.

ACTIVE SUBSTANCES: 0.3–0.7% of etherical oil, most represented ingredient is in general bornyl acetate, but other sesquiterpenes are also present: β-caryophyllene, valerenal, valeranon.

Carefully dried roots (40° C.) contain 0.5–2% of valepotriate (valerian epoxy-triester), bicyclic iridoid-monoterpene. There are most valtrates and isovaltrates. dihydrovaltrate and IVHD-valtrate (isovaleryl-oxyhydroxydidrovaltrate).

Valeric acid and acetoxyvaleric acid (0.8–0.3%) are characteristic ingredients of the officinal drug—they are not found in other kinds of valerian.

The root contains a very small percentage (0.01–0.05%) of alcaloids such as valerianin and x-methylpyril-ketone.

INDICATIONS: sedative effect (etheric oil, valepotriats), spasmolytic and muscle relaxant (valeric acid). Valeric acid and related sesquiterpenes inhibit degradation of an important neurotransmitter γ-aminoteraxaci acid. Tea from valerian root is used for calming, relaxation, then, in case of nervous tenseness, difficulties with sleeping (but only as an auxiliary, and not as a sleep-inducing agent) and the state of stress. On the other hand, valepotriats or tinctures standardized according to the requests of valepotriats (usually 50 mg per dose) are used as tranquilizers and timoleptics. Such preparations which always contain a mixture of valepotriats are mostly made from other kinds of valerian. *Valenana edulis* NUTT.ssp.MEYER—Mexican valerian or *Valeriana wallichii* DC.—Indian valerian. They usually contain a high percentage of dihrovaltrates and isovaltrates. Such preparations are used for healing of psychomotoric and psychosomatic difficulties, in case of stress or anxious states, and in case of reduced concentration.

Further text of the description of the invention is almost completely concentrated only on the medicament obtained from the herbal composition presented in Table 2.

Regarding the medicament, i.e. tea, a herbal tincture and a pill, obtained from the herbal composition, presented in Table 2, the following can be said:

The medicament has a very strong hypoglycemic effect, comparable to that of insulin, so that the recommended doses should be strictly observed. Generally speaking, the concentration of glucose in blood could be reduced even by 6 mmol/l to 8 mmol/l daily, but that should be avoided because of the danger of hypoglycemic coma.

It was noticed that this medicament also reduces the level of cholesterol at the same time. Also, it restores the disturbed metabolism of carbohydrates and fats. Furthermore, it removes all the visible symptoms of manifested diabetes mellitus type II. Among other things, it restores physical strength. It heals diabetes II when other antidiabetics are already weak. Consequences harmful for health have not been noticed. The medicament is effective even without a strict diabetic diet. A further advantage of this herbal tincture, which should be pointed out in particular, is the fact that women can use it even during pregnancy. It was noticed, however, that consuming nicotine, alcohol and caffeine reduces the effectiveness of the medicament and causes the prolongation of the treatment; consumed in extreme quantities, they particularly unfavourably effect the treatment.

Preparation, Dosing and the Way of Application
Preparation of the Tea

According to the invention, the tea from the herbal composition is obtained by this process: The herbal composition, made of dried and cut ingredients according to Table 1 or Table 2, is to be covered with boiling water, where the mass of the herbal composition and the mass of water are in the proportion 1–2:75. Then it should be left to rest in a covered container for 20 minutes, and then it should be filtered.

The above proportion of masses corresponds to covering of 1–2 spoonfuls of the herbal composition with 3 dl of boiling water.

Dosing and the Way of Application of the Tea
(Refers Only to the Tea Obtained from Herbal Mixture Presented in Table 2)

An aggressive starting daily dose is recommended: three times a day, half an hour before eating, a dose of the tea prepared from 2 spoonfuls of the herbal composition and 3 dl of water should be taken (that is, 3×(2×4 g)/3 dl/day, i.e. 24 g/9 dl/day). The tea should be taken immediately after it is prepared.

Through experiments, both on volunteers, and on rodents, it was ascertained that excellent results are achieved already by the tea itself, in case concentrations which are not so hightened in relation to its normal value are in question.

Preparation of the Herbal Tincture

According to the invention, the herbal tincture from the herbal composition is obtained in the following way: the herbal composition which is made of dried and cut ingredients according to Table 1 or Table 2 is to be covered in 60% ethanol at the room temperature, whereby on 1 kg of the herbal composition 7.21 l 60% ethanol are to be used. For the purpose of extraction, the mixture is left to rest for 28 days in a covered container, at the room temperature and pressure. The herbal tincture is then obtained by decanting the liquid above the sediment.

Dosing and the Way of Application of the Herbal Tincture
(Refers Only to the Herbal Tincture Obtained from Herbal Mixture Presented in Table 2)

An aggressive starting daily dose is recommended: three times a day 1 spoonful of the herbal tincture (3×10 ml/day), through first two days of treatment. On the third day, and on, 1 spoonful of the herbal tincture (2×10 ml/day) should be taken twice a day. Furthermore, with all the concentrations of glucose in blood above 8 mmol/l, it is recommended to take the tea and the herbal tincture. The optimum speed of the reduction of the concentration of glucose in the blood is, approximately, from ¼ mmol/l up to ½ mmol/l, that is, averagely ⅓ mmol/l daily. When the level of glucose in the blood drops to approximately 7 mol/l, for maintaining of that level, only a teaspoonful of the herbal tincture (5 ml/day) daily is sufficient. If the patient already uses angidiabetics in the moment when the treatment by this method is started, then, on the third day of the treatment by the combined therapy (tea+herbal tincture), in case the level of glucose in the blood starts falling by ⅓ mmol/l daily, taking of the antidiabetic used can start being reduced at the rate of half a pill each two days. In case that the patient takes 4 pills of Euglucon daily, the daily treatment lasts twice longer. Sometimes Euglucon cannot be completely left out, so that it remains in use, but in a reduced extent.

Preparation of the Pill

According to the invention, the active substance for the pill from the herbal composition is obtained according to the following process: the herbal composition, made of dried and cut ingredients according to Table 1 or Table 2, is dissolved in 60% ethyl alcohol. For the purpose of obtaining the alcoholic tincture, the mixture is left to rest for 28 days, in a dark place, at the room temperature and pressure. The alcoholic tincture obtained in that way was exposed to evaporation in the vacuum of 10 mmHg in the timely linear temperature gradient from 20° C. to 40° C. during the time of 30 minutes. The quantity of 50 ml alcoholic tincture was mixed with 0.5 g of nonionogenic co-solubilizer of hydrophilic tenside (e.g. sorbitol) which has a capability of keeping parts of lipophilic components of alcoholic tincture in the water solution and solubilize them for peroral application. After 40 minutes, in timely linear temperature gradient from 20° C. to 40° C., also during the time of 30 minutes, the density of the tincture is increased by the factor of 10. The still dense suspension obtained from the alcoholic tincture in that way was immediately frozen by liquid air to the temperature of −186° C. and lyophilized in high vacuum of 0.001 mmHg into fine powder. This fine powder is an active substance which is used for production of the pill. It meets the basic conditions for pilling, because the experiments on animals showed that the high pressure, which can cause the plastic deformation of particles and the deformation of intramolecular forces, did not disturb its biological activity.

According to the invention, from the powder obtained by the technological process described above, the pill was prepared in the following way: 60 mg of the active substance in form of fine powder, which contains all the ingredients of the extracted herbal composition, is mixed with 180 mg of the natural zeolite, which is tribo-activated and in a microcrystalic form, very stable and with the pH-value from 1 to 11. For the purpose of balancing and better compressibility, to the mixture obtained in such a way, 35.0 mg of monosaccharides was added. The mixture made in such a way was mixed with the natural clarified microcellulose in the dose of 80 mg, which allows plastic deformation. After that, Mg-stearate in the dose of 5.0 mg was added, for obtaining of a better slipping quality. The quantity content of the pill is clearly shown in Table 3. The homogenous mixture prepared in such a way was compressed by the method of direct compressing, which is the method of choice for pilling of moisture sensitive and thermolabile curative substances.

TABLE 3

| Active substance | 60.0 mg | 16.7% by wt. |
|---|---|---|
| Natural microcellulosis | 80.0 mg | 22.2% by wt. |
| Natural zeolite | 180.0 mg | 50.0% by wt. |
| Monosaccharides | 35.0 mg | 9.7% by wt. |
| Mg-stearat | 5.0 mg | 1.4% by wt. |
| In all: | 360.0 mg | 100.0% by wt. |

Dosing and the Way of Application of the Pill
(Refers Only to the Pill Obtained from the Herbal Composition Presented in Table 2)

In numerous experiments on volunteers it was ascertained that, on the average, for a person suffering from diabetes mellitus type II, about 0.7–1.0 mg/kg of body weight/day of the active substance was necessary according to the invention.

More concretely, in case that a person suffering from diabetes mellitus type II has the glucose level up to 10 mmol/l, the therapy of 2 pills a day is recommended, and that, one pill in the morning before a meal, and the other in the evening, also before a meal.

However, in case that a person suffering from diabetes mellitus type II has the glucose level above 10 mmol/l, the therapy of 3 pills a day is recommended, one before the meal in the morning, at noon and in the evening.

In both cases a moderate diet and physical activity are understood.

Experiments have shown that it is possible to lower the level of glucose in the blood of an ill person even by 3–4 mmol/l in only one day, but that should be avoided because of the danger of falling in a hypoglycemic coma. It should particularly be pointed out that the use of the pill made according to the invention enables the reduction of the daily dose of used classical antidiabetics, as is the case also with the tea and the tincture.

This invention will be explained in greater detail by examples described below which all refer to the application of the tea, the herbal tincture and the pill obtained exclusively from the herbal composition presented in Table 2. However, the purpose of these examples is not to limit the scope of the invention. The first series of examples refers to testing of the invention on volunteers, in which the first three examples refer to cases in which a considerable reduction of the concentration of glucose in the blood was successfully achieved only with the help of the combined therapy (the tea+the herbal tincture). After that, the presentation of the testing of this invention carried out on rodents follows.
Pharmacological Data for the Tea and the Herbal Tincture
The Presentation of the Results of the Testing Carried out on Volunteers

EXAMPLE 1

A man, aged 50, with diagnosed diabetes mellitus type II, with 15.58 mmol/l of glucose in the blood, through the first three days of treatment, drank three times a day, half an hour before a meal, a dose of tea prepared from 2 spoonfuls of herbal composition and 3 dl of water (that is, 3×(2×4 g)/3 dl/day, i.e. 24 g/9 dl/day). On the fourth day, and onwards, the patient drank the upper dose twice a day, in the morning and in the evening, half an hour before a meal (that is, 2×(2×4 g)//3 dl/day, i.e. 16 g/6 dl/day). After 29 days of treatment, glucose in blood dropped to 8.02 mmol/l. By further therapy of 1 teaspoonful of the herbal tincture daily (5 ml/day), the level of the glucose in the blood was maintained. It should be particularly pointed out here that, parallelly with the tea made according to this invention, no other antidiabetic was used for the purpose of reducing the level of glucose in the blood. During the treatment, the patient was on a very moderate diet, and he was physically moderately active.

EXAMPLE 2

A woman, aged 45, with diabetes mellitus type II, with previous therapy of 2 pills of Euglucon a day, had an approximately stable level of 8 mmol/l of glucose in the blood. Through the first three days of treatment, the patient drank three times daily, half an hour before a meal, a dose of tea prepared from 2 spoonfuls of the herbal composition and 3 dl of water (that is, 3×(2×4 g)/3 dl/day, i.e. 24 g/9 dl/day).

Starting with the fourth day, and conclusively with the fifteenth day of the therapy, the pacient drank the dose mentioned above twice a day, in the morning and in the evening, half an hour before a meal. Simultaneously, taking of Euglucon was reduced at the speed of ½ pill per day. After fifteen day of the therapy in all, the level of glucose in the blood fell to 7 mmol/l, and taking of Euglucon was completely left out. With a further therapy of 1 teaspoonful of the herbal tincture daily (5 ml/day) that level of glucose in the blood was maintained. During the testing, the patient was on a moderate diet, and she was physically moderately active.

EXAMPLE 3

A man, aged 52, with expressed symptoms of diabetes mellitus type II, in the beginning of the therapy he had the concentration of glucose in the blood of 9 mmol/l. He did not take any antidiabetic. During the first three days of treatment, the patient drank the tea made from 2 spoonfuls of the herbal composition and 3 dl of water (that is, 3×(2×4 g)/3 dl/day, i.e. 24 g/9 dl/ day) three times a day, half an hour before a meal. Starting with the fourth day, and conclusive with the fourteenth day of treatment, the patient drank the tea made in the way described above twice a day, in the morning and in the evening, half an hour before a meal (that is, 2×(2×4 g)/3 dl/day, i.e. 16 g/6 dl/day). After fourteen days of the therapy in all, the concentration of glucose in the blood fell to 6 mmol/l. That level of glucose in the blood was maintained by taking of 1 teaspoon of the herbal tincture daily (5 ml/day). The patient was physically moderately active and he was on a very weak diet.

EXAMPLE 4

A man, aged 60, with diagnosed diabetes mellitus type 1i, with the concentration of glucose in the blood of 12.0 mmol/l, was taking 2 pills of Euglucon a day before the therapy. During the first two days of treatment, the patient drank 10 ml of the herbal tincture a day (30 ml/day) three times a day and a dose of the tea made from 2 spoonfulls of the herbal composition and 3 dl of water (that is, 3×(2×4 g)13 dl/day, i.e. 24 g/9 dl/day). On the third day, the daily doses, both, of the tea, and of the herbal tincture, were reduced by a dose, so that the patient continued drinking 10 ml of the herbal composition (20 ml/day) twice a day, and a dose of the tea made in the way mentioned above twice a day, in the morning and in the evening, half an hour before a meal (16 g/6 dl/day). The daily dose of Euglucon was gradually reduced. After the fifteen days of treatment in all, the level of glucose in the blood fell to 7.0 mmol/l, and the daily dose of Euglucon was reduced to 1 pill. The achieved level of glucose in the blood was maintained ba the therapy consisting of 1 teaspoon of the herbal tincture daily (5 ml/day) or of one dose of the tea made in the way described above (2×4 g/3 dl/day).

EXAMPLE 5

A man, aged 50, with clearly evident diabetes mellitus type II, with the concentration of glucose in the blood of 16.19 mmol/l and cholesterol 7.37 mmol/l before the beginning of the treatment according to this invention. During the first two days of treatment the patient drank 10 ml of the herbal tincture (30 ml/day) and three times a day, half an hour before a meal, a dose of the tea made from 2 spoonfuls of the herbal composition and 3 dl of water (that is, 3×(2×4 g)/3 dl/day, i.e. 24 g/9 dl/day). On the third day daily doses, both, of the tea, and the herbal tincture, were reduced by one dose, so that the patient kept on drinking 10 ml of the herbal tincture (20 ml/day) twice a day, and a dose of the tea prepared in the way described above twice a day, in the morning and in the evening, half an hour before a meal (16 g/6 dl/day). After fifteen days of treatment in all, the level of glucose dropped to 9.98 mmol/l, and cholesterol was reduced to 4.41 mmol/l. The achieved level of glucose in the blood was maintained by the therapy consisting of 1 teaspoon of the herbal tincture daily (5 ml/day) or one dose of tea made in the way described above (2×4 g/3 dl/day).

EXAMPLE 6

A man, aged 48, with diagnosed diabetes mellitus type II, with the level of glucose in the blood of 17.0 mmol/l, did not use any antidiabetics when he started the therapy. During the first two days of the treatment, the patient drank 10 ml of the herbal tincture (30 ml/day) three times a day and one dose of the tea prepared from 2 spoonfulls of the herbal composition and 3 dl of water (that is, 3×(2×4 g)/3 dl/day, i.e. 24 g/9 dl/day) three times a day. On the third day, daily doses, both, of the tea, and of the herbal tincture, were reduced by one dose, so that the patient continued drinking 10 ml of the herbal tincture (20 ml/day) twice a day, and one dose of of the tea prepared in the way described above twice a day, in the morning and in the evening, half an hour before a meal (16 g/6 dl/day). After fifteen days of treatment in all, the level of glucose in the blood dropped to 9.8 mmol/l. The achieved level of glucose in the blood was maintained by therapy consisting of 1 teaspoon of the herbal tincture daily (5 ml/day) or one dose of the tea prepared in the way described above (2×4 g/3 dl/day).

EXAMPLE 7

A man, aged 52, with diagnosed diabetes mellitus type II, with a preliminary therapy of 4 pills of Euglucon daily, had the level of glucose in the blood of 16.0 mmol/l. During the first two days of the treatment, the patient drank 10 ml of the herbal tincture (30 ml/day) and a dose of the tea prepared from 2 spoonfulls of the herbal composition and 3 dl of water (that is, 3×(2×4 g)/3 dl/day, i.e. 24 g/9 dl/day) three times a day. On the third day, daily doses, both, of the tea, and of the herbal tincture, were reduced by one dose, so that the patient continued drinking 10 ml of the herbal tincture (20 ml/day) twice a day, and one dose of of the tea prepared in the way described above twice a day, in the morning and in the evening, half an hour before a meal (16 g/6 dl/day). After only fifteen days of treatment, the level of glucose in the blood dropped to 12.0 mmol/l, and the daily dose of Euglucon was reduced to 0 pills. It should particularly be pointed out here that with the daily dose of four pills, Euglucon is harmful for the kidneys, and the patient was bound for imminent taking of insulin.

Toxicology

No toxic effects were ascertained in the testings mentioned above. The physical status of examined persons showed no sign of any harmful reaction to treatment.

The Presentation of the Results of the Experiments Carried Out on Rodents

The effect of the perparation made according to this invention on the level of glucose in diabetic mice with respect to the time of probing was studied. All doses which were applied on rodents were adjusted to the concentration of proteins in the preparation made according to the invention. The concentration of proteins in the preparation made according to the invention was determined by the method by Bradford. To the determination of the concentration of proteins were subjected the tea, the tincture (after the elimination of alcohol), and the lyophilized sample. The concentration of glucose in CBA diabetic mice (18 mice per group) before the treatment with the preparation made according to the invention on the average amounted to 22.4±6.5 mmol/l. After 10 minutes, that is 30 minutes, the concentration of glucose in mice started to fall, and after 2 hours from the application of the preparation, the concentration of glucose was on the average by over 20% lower from the starting value. The results obtained by the application of the preparation in form of an alcoholic tincture, non-alcoholic tincture, that is, a pill are presented in FIG. 1.

Now follows, as a supplement, the presentation of the results of testing of the toxicity of the tea and the tincture prepared according to the invention.

In order to check the toxicity of the preparation made according to the invention (the tea and the tincture), mice were receiving it daily in food in the amount of 20 mg/kg body weight/day.

According to the protocol of the research and ascertaining of the toxicity, each 14 days the mice spent 24 hours in metabolic cages (Table 4). During the 24 hours, the quantity of the eaten food, the drunk water, the excreted urine and feces was measured. From the results obtained it turns out that during the 24 hours, on the average, one mouse ate about 5.37±1.08 g of food, drunk 2.94±1.02 ml of water and excreted 1.14±0.28 g of feces, and urinated 1.2±0.4 ml of urine.

TABLE 4

| Group of mice | Food (g) | Water (ml) | Feces (g) | Urine (ml) |
|---|---|---|---|---|
| Control | 21.2 ± 1.5 | 22.4 ± 2.2 | 7.8 ± 0.4 | 6.2 ± 0.2 |
| 30th day | 22.8 ± 1.9 | 17.3 ± 1.8 | 4.9 ± 0.6 | 7.5 ± 0.5 |
| 60th day | 21.0 ± 0.9 | 15.6 ± 2.3 | 4.6 ± 0.9 | 5.8 ± 0.1 |
| 90th day | 33.1 ± 2.5 | 15.9 ± 1.9 | 4.5 ± 0.5 | 6.4 ± 0.3 |
| 120th day | 29.7 ± 1.8 | 16.4 ± 2.5 | 6.5 ± 0.6 | 5.0 ± 0.4 |
| 150th day | 29.3 ± 0.9 | 17.9 ± 2.1 | 8.2 ± 1.2 | 7.0 ± 0.6 |
| 180th day | 33.0 ± 2.4 | 15.8 ± 1.8 | 7.9 ± 1.1 | 6.2 ± 0.4 |

REMARK

Here and below, the data are presented as the average value ± the standard deviation.

Each 14 days urine was collected and analysed (Table 5). With the duration of the testing, that is, during the experiment there was no appearance of glucose, bilirubin or ketonic bodies of urine in the tested mice. Erythrocytes, urobilinogen, nitrites or leucocytes were also not present. Small presence of proteins was actually the result of technical difficulties during the separation of urine from the remains of food. The contamination of urine with the remains of food is possible.

TABLE 7-continued

| | 24 h | 7 days | 3 months | 6 months |
|---|---|---|---|---|
| Creatinine (μmol/l) | 42.5 ± 1.2 | 51.7 ± 4.2 | 46.3 ± 2.5 | 41.4 ± 1.9 |
| AST (u/l) [22° C.] | 54.9 ± 12.5 | 78.1 ± 10.9 | 56.2 ± 9.9 | 55.2 ± 12.3 |
| ALT (u/l) [22° C.] | 26.2 ± 3.4 | 29.0 ± 2.0 | 28.6 ± 3.5 | 29.4 ± 4.6 |
| Cholesterol (mmol/l) | 2.6 ± 0.2 | 3.1 ± 0.7 | 2.8 ± 0.4 | 3.3 ± 0.4 |

TABLE 5

| Groups of mice | Glucose in urine (g/dl) | Bilirubin | Ketones (mg/μl) | Specific weight (g/ml) | Erythrocytes (number of cells/μl) | pH | Proteins (mg/dl) | Urobilinogen (mg/dl) | Nitrites | Leucocytes (no. of cells/μl) |
|---|---|---|---|---|---|---|---|---|---|---|
| Control | – | – | – | 1.030 | – | 7.0 | ++ | – | – | – |
| 30th day | – | – | – | 1.020 | – | 6.5 | ++ | – | – | – |
| 60th day | – | – | – | 1.030 | – | 6.5 | ++ | – | – | – |
| 90th day | – | – | – | 1.020 | – | 7.0 | + | – | – | – |
| 120th day | – | – | – | 1.030 | – | 6.5 | + | – | – | – |
| 150th day | – | – | – | 1.020 | – | 7.0 | ++ | – | – | – |
| 180th day | – | – | – | 1.020 | – | 7.0 | + | – | – | – |

During the acute, subchronical and chronical experiments, the animals which were receiving the mixture of plants from this invention were sacrificed. The serum obtained was analyzed and a number of biochemical parameters which characterize various damages of vital organs in the body, and the function of metabolism in the body were tested. Only some parameters were presented, and that: urea, creatinine, AST, ALT, cholesterol. The results show that particular biochemical parameters in mice which were receiving the preparation made according to this invention had no deviation from the control values (Table 6 and Table 7).

Analysis of the Serum of Mice Treated According to the Invention

TABLE 6

| | 24 h | 7 days | 3 months | 6 months |
|---|---|---|---|---|
| Urea mmol/l | 7.7 ± 0.7 | 7.1 ± 0.8 | 6.8 ± 1.3 | 6.8 ± 0.3 |
| Creatinine (μmol/l) | 47.0 ± 1.8 | 50.3 ± 1.6 | 48.5 ± 2.9 | 40.8 ± 2.2 |
| AST (u/l) [22° C.] | 70.6 ± 11.9 | 122.6 ± 10.3 | 76.4 ± 11.4 | 53.3 ± 11.6 |
| ALT (u/l) [22° C.] | 26.6 ± 2.7 | 25.7 ± 3.1 | 29.3 ± 4.2 | 27.8 ± 6.5 |
| Cholesterol (mmol/l) | 2.3 ± 0.3 | 3.1 ± 0.4 | 3.4 ± 0.5 | 3.2 ± 0.3 |

Analysis of the Serum of the Control Mice

TABLE 7

| | 24 h | 7 days | 3 months | 6 months |
|---|---|---|---|---|
| Urea (mmol/l) | 7.6 ± 0.5 | 8.3 ± 0.8 | 7.4 ± 0.4 | 7.2 ± 0.5 |

Pharmacological Data for the Pill

The effectiveness of the pill regarding the hypoglycemic effect was ascertained on diabetic mice. Diabetes was caused by a single injection of Alloxan (75 mg/mouse/kg of body weight). 14 days later, all the diabetic mice were included in the experiment. A zero sample of blood was taken from diabetic mice and the quantity of glucose in the blood was measured, which is shown in Table 8 and FIG. 2 as 100%. The preparation of the pill was introduced by a probe to diabetic mice, per os, in the dose of 20 mg of the active substance/mouse/kg of body weight. In the first 30 minutes, the concentration of glucose in the periferal blood of the treated diabetic mice was reduced on the average by about 11% (Table 8). After the next 30 minutes, the total decline of the concentration of glucose amounted to over 18%, and after the next 60 minutes, i.e. after 120 minutes, the total decline of the concentration of glucose by about 30% was measured in some mice. The results are shown in Table 8. These results point out to the positive hypoglycemic effect, i.e. the decline of the concentration of glucose by 10 to 30% from its starting value, ascertained on laboratory mice, which were classified in groups of 12 mice.

TABLE 8

| Group of mice | 0 min; % of starting value | 30 min; % of starting value | 60 min; % of starting value | 120 min; % of starting value |
|---|---|---|---|---|
| 1. | 100 | 92.5 ± 4.2 | 78.5 ± 4.3 | 72.4 ± 5.2 |
| 2. | 100 | 88.6 ± 4.0 | 79.3 ± 3.9 | 70.2 ± 6.8 |
| 3. | 100 | 82.5 ± 3.5 | 74.9 ± 3.6 | 73.5 ± 6.2 |
| 4. | 100 | 94.1 ± 3.1 | 85.7 ± 4.1 | 80.1 ± 5.5 |
| 5. | 100 | 88.9 ± 3.5 | 82.7 ± 3.5 | 78.4 ± 5.9 |
| 6. | 100 | 91.0 ± 4.1 | 85.4 ± 4.2 | 77.5 ± 5.0 |
| 7. | 100 | 82.3 ± 4.2 | 79.8 ± 4.5 | 83.4 ± 5.8 |
| 8. | 100 | 90.5 ± 3.6 | 84.3 ± 3.2 | 82.6 ± 5.3 |
| 9. | 100 | 86.4 ± 4.6 | 83.2 ± 4.0 | 89.5 ± 6.6 |

TABLE 8-continued

| Group of mice | 0 min; % of starting value | 30 min; % of starting value | 60 min; % of starting value | 120 min; % of starting value |
|---|---|---|---|---|
| 10. | 100 | 93.5 ± 4.0<br>89.3 ± 4.2 | 87.4 ± 3.8<br>82.1 ± 4.0 | 85.4 ± 6.7<br>79.3 ± 6.1 |

Figure 2:
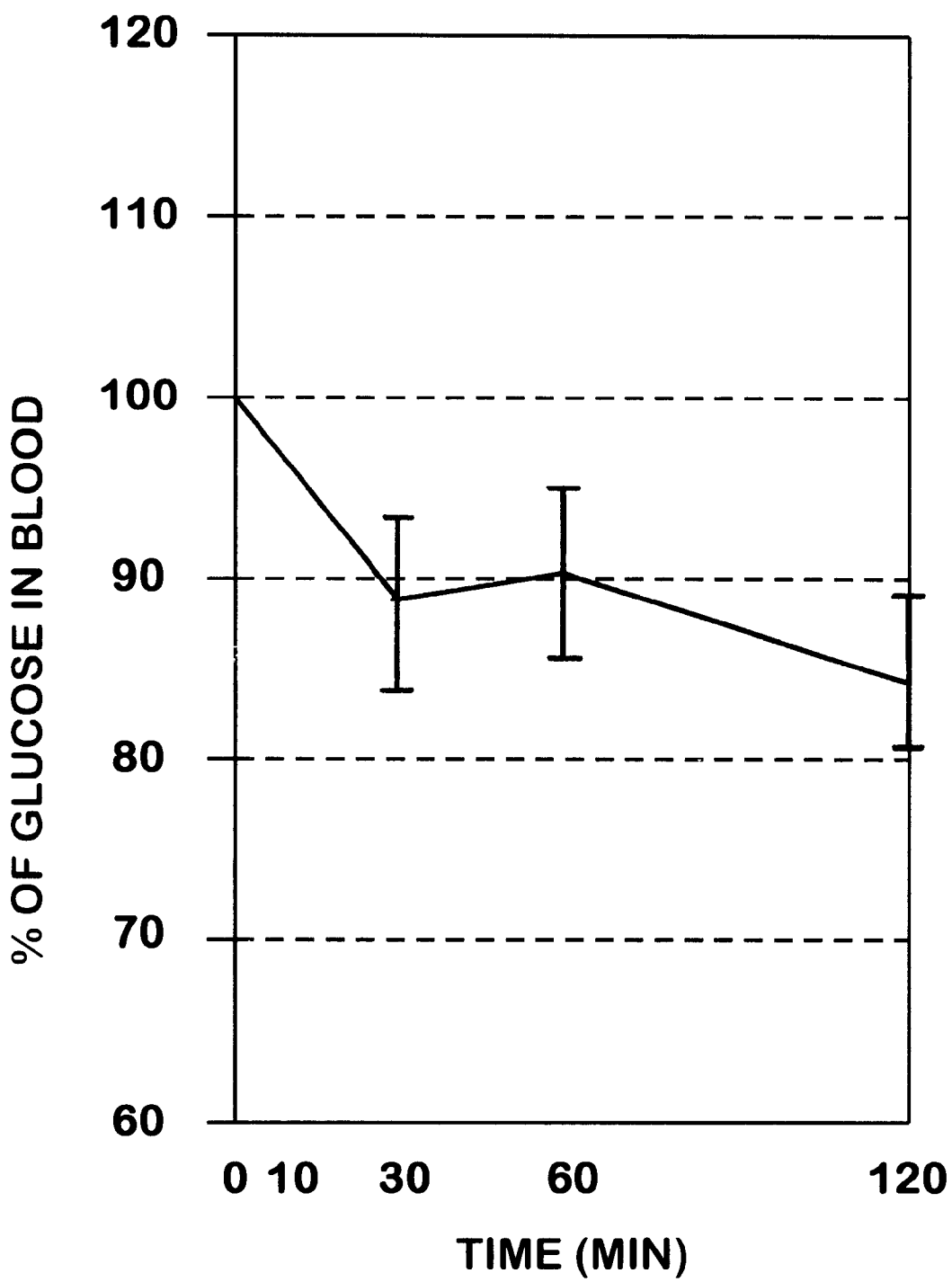
FIG. 2. is a graph showing decreasing glucose concentration in mice with induced diabetes and treatment with herbal preparation.

In the repeated experiment, the result of which is shown in FIG. 2, the decline of the conentration of glucose in the peripheral blood of the diabetic mice was noticed, and that by over 20%, after 120 minutes.

Figure 3:
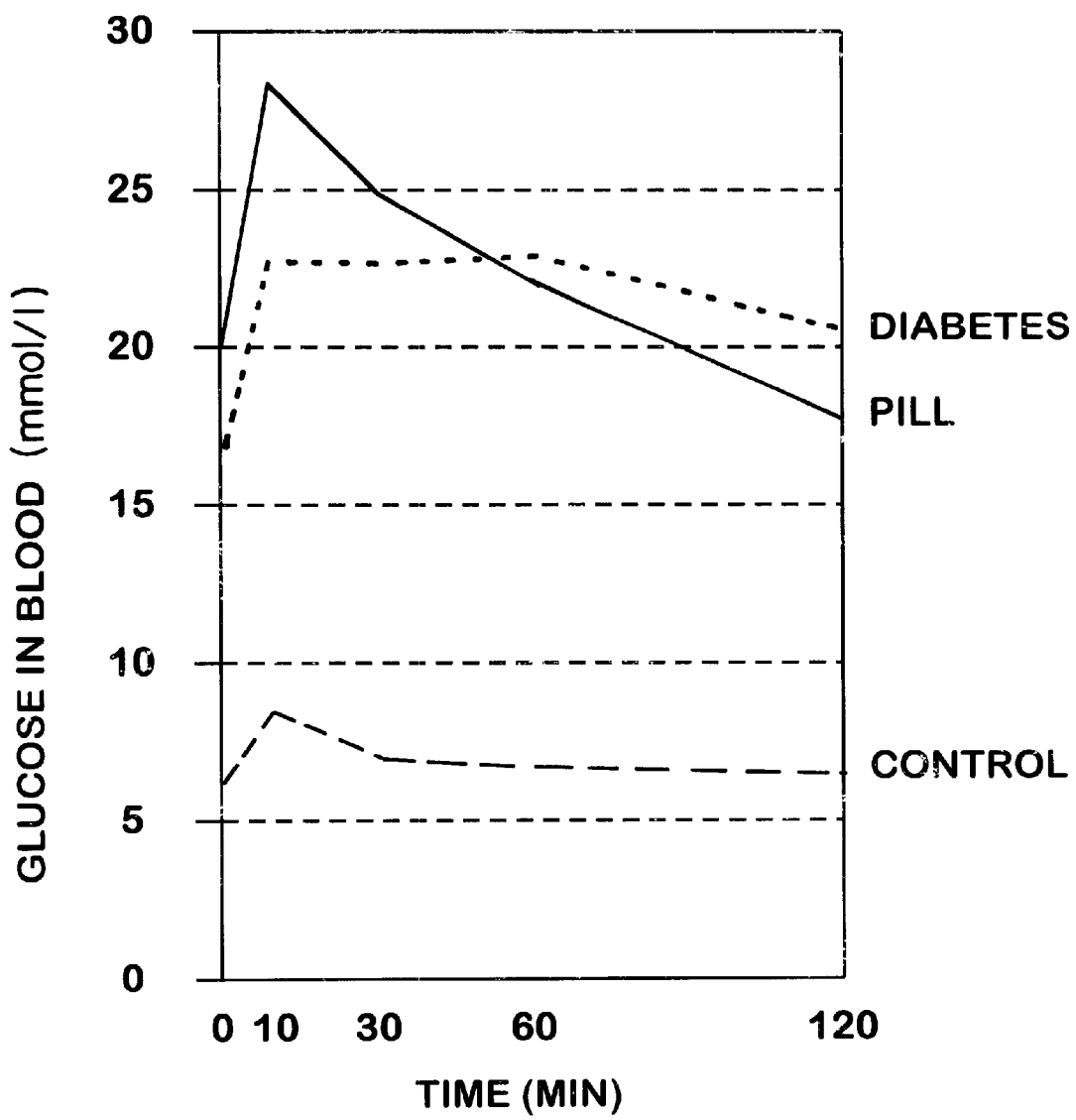
FIG. 3. is a graph showing concentration of glucose in blood of NOD mice after treatment with herbal preparation.

Testings were also carried out on NOD mice. NOD mice are a kind of mice in which diabetes was developed spontaneously. The results of the test of assimilation of glucose are presented in FIG. 3. It shows that, after 120 minutes, the diabetic mice fed with the preparation of the pill according to the invention had a considerably reduced concentration of glucose in the peripheral blood in relation to the control diabetic mice, designated with "Diabetes". The designation "Control" in FIG. 3 refers to non-diabetic mice.

Next is given, as an enclosure, the presentation of the testing of toxicity of the pill prepared according to this invention.

In experiments on healthy mice of the kind CBA/H Zgr of both sexes during the next 6 moths, various parameters were controlled which were anticipated regarding evenutal toxicity of the preparation which was daily added to the food for laboratory mice in the quantity of 5 mg of the active substance per one gram of food. During these experiments, variations of the body mass of mice was observed on the days: $7^{th}$, $14^{th}$, $30^{th}$, $60^{th}$, $120^{th}$ and $180^{th}$ from the beginning of such diet. On those days the mice were placed in the metabolic cage during 24 hours, which enabled the determination of the quantity of food eaten by each mice, the quantity of water drunk, and the mass of feces and the volume of the excreted urine. The results are shown in Table 9 and from them it is evident that the application of the preparation according to the invention did not disturb the health of treated mice during 6 months.

TABLE 9

| Group of mice | Food (g) | Water (ml) | Feces (g) | Urine (ml) |
|---|---|---|---|---|
| Control | 23 ± 1.3 | 24 ± 2.4 | 5 ± 0.4 | 6 ± 0.2 |
| $30^{th}$ day | 19 ± 2.4 | 20 ± 1.7 | 6 ± 0.6 | 9 ± 0.4 |
| $60^{th}$ day | 24 ± 0.9 | 20 ± 1.5 | 6 ± 0.5 | 7 ± 0.1 |
| $90^{th}$ day | 27 ± 1.5 | 18 ± 3.1 | 5 ± 0.7 | 5 ± 0.1 |
| $120^{th}$ day | 30 ± 2.1 | 19 ± 2.1 | 7 ± 1.1 | 6 ± 0.2 |
| $150^{th}$ day | 31 ± 2.5 | 18 ± 2.6 | 9 ± 0.7 | 5 ± 0.4 |
| $180^{th}$ day | 35 ± 1.2 | 19 ± 2.1 | 8 ± 0.8 | 7 ± 0.5 |

At the same time, a sample of urine was taken from each mouse, in which parameters which would eventually point out to negative, harmful effects were determined, the results of which are presented in Table 10. The results of monitoring 10 different parameters point out to innocuousness of this preparation.

TABLE 10

| Groups of mice | Glucose in urine (g/dl) | Bilirubin | Ketones (mg/µl) | Specific weight (g/ml) | Erythrocytes (number of cells/µl) | pH | Proteins (mg/dl) | Urobilinogen (mg/dl) | Nitrites | Leucocytes (no. of cells/µl) |
|---|---|---|---|---|---|---|---|---|---|---|
| Control | − | − | − | 1.020 | − | 6.5 | − | − | − | − |
| $30^{th}$ day | − | − | − | 1.030 | − | 7.0 | − | − | − | − |
| $60^{th}$ day | − | − | − | 1.030 | − | 6.5 | − | − | − | − |
| $90^{th}$ day | − | − | − | 1.020 | − | 7.0 | − | − | − | − |
| $120^{th}$ day | − | − | − | 1.030 | − | 6.5 | − | − | − | − |
| $150^{th}$ day | − | − | − | 1.030 | − | 6.5 | + | − | − | − |
| $180^{th}$ day | − | − | − | 1.020 | − | 7.0 | + | − | − | − |

After the $180^{th}$ day the mice were sacrificed in ether narcosis, various organs were taken out of them and they were subjected to histological processing and later detailed examination under the light microscope. No pathological changes on the examined organs, both, on the control ones, and on those from the mice fed with the invention prepared in form of a pill.

After adding of all the ingredients of the pill to the food, the healthy mice were daily fed with such a mixture i the quantity of about 20 mg of the active substance per mouse. In this group of mice the tests already stated above were simultaneously carried out as well, which, as those with mice which were taking food without the added pill for a long time, showed that there were no toxic consequences of the application of pills during 6 months period and at the end of it. The results are presented in Table 11. The results show that there were no changes in the concentration of the measured parameters during 6 months (Table 11). The value of aspartate amino transferase was somewhat raised during the first 7 days, which can be explained by adjustment of the mice to the new type of diet (maybe a little hunger was present during the first 7 days). But, after 6 months there are no sings of changes (Table 11).

Analysis of the Serum of Mice Treated According to the Invention

TABLE 11

| | 1 day | 7 days | 3 months | 6 months |
|---|---|---|---|---|
| Urea (mmol/l) | 7.4 ± 0.7 | 7.5 ± 0.8 | 7.1 ± 1.3 | 6.5 ± 0.3 |
| Creatinine (µmol/l) | 47.0 ± 1.8 | 48.3 ± 1.4 | 46.5 ± 2.9 | 45.8 ± 2.8 |
| AST (u/l) [22° C.] | 90.6 ± 13.1 | 112.6 ± 12.3 | 86.4 ± 10.4 | 57.3 ± 13.7 |

TABLE 11-continued

| | 1 day | 7 days | 3 months | 6 months |
|---|---|---|---|---|
| ALT (u/l) [22° C.] | 26.3 ± 3.7 | 27.7 ± 3.1 | 28.3 ± 4.2 | 26.8 ± 7.5 |
| Cholesterol (mmol/l) | 2.8 ± 0.1 | 3.0 ± 0.5 | 3.7 ± 0.4 | 3.9 ± 0.3 |

Values of corresponding parameters of serum of the control mice are given in Table 12.

Analysis of the Serum of the Control Mice

TABLE 12

| | 1 day | 7 days | 3 months | 6 months |
|---|---|---|---|---|
| Urea (mmol/l) | 6.6 ± 0.6 | 8.5 ± 0.8 | 7.6 ± 0.3 | 7.0 ± 0.8 |
| Creatinine (μmol/l) | 44.5 ± 1.0 | 51.2 ± 4.1 | 46.5 ± 2.4 | 40.4 ± 2.3 |
| AST (u/l) [22° C.] | 53.9 ± 17.5 | 78.5 ± 11.9 | 58.9 ± 8.9 | 54.2 ± 12.7 |
| ALT (u/l) [22° C.] | 27.2 ± 2.4 | 28.0 ± 1.9 | 27.6 ± 3.1 | 28.4 ± 4.5 |
| Cholesterol (mmol/l) | 2.5 ± 0.3 | 3.0 ± 0.7 | 2.7 ± 0.6 | 3.2 ± 0.4 |

In the end, it should be pointed out that, while the invention which has herein been shown and described in what is presently concieved to be the most practical and preferred embodiment thereof, it will be apparent to those of ordinary skill in the art that many modifications may be made thereof within the scope of the invention, which scope is to be accorded the broadest interpretation of the appended claims, so as to encompass all equivalent methods and products.

What is claimed is:

1. An herbal composition consisting of the following dried ingredients:

| | |
|---|---|
| plant of centaury (*Centaurii umbellatum*, Gentianaceae) | 10–15% by wt. |
| root of dandelion (*Teraxaci officinale, asteraceae*) | 6–12% by wt. |
| fruit of juniper (*Juniperi communis L, Cupresaceae*) | 5–8% by wt. |
| plant of nettle (*Urticae dioica L, Urticeae*) | 5–10% by wt. |
| root of nettle (*Urticae dioica L, Urticaceae*) | 5–10% by wt. |
| root of chicory (*Cichorium intybus L, Cichoriaceae*) | 12–20% by wt. |
| leaf of black mulberry (*Morus nigra L, Moraceae*) | 5–10% by wt. |
| flower of yarrow (*Achilleae millefolium L, Asteraceae*) | 2–5% by wt. |
| leaf of bilberry (*Vaccinium myrtillus L, Ericaceae*) | 4–10% by wt. |
| pod of beans (*Phaseolus vulgaris L, Fabaceae*) | 10–20% by wt., and |
| root of valerian (*Valeriana officinalis L, Valerlanaceae*) | 5–10% by wt., | wherein each percentage refers to the total mass of the dried ingredients in the composition.

2. An herbal composition consisting of the following dried ingredients:

| | |
|---|---|
| plant of centaury (*Centaurii umbellatum*, Gentianaceae) | 12.3% by wt. |
| root of dandelion (*Teraxaci officinale, asteraceae*) | 9.7% by wt. |
| fruit of juniper (*Juniperi communis L, Cupresaceae*) | 6.2% by wt. |
| plant of nettle (*Urticae dioica L, Urticeae*) | 7.4% by wt. |
| root of nettle (*Urticae dioica L, Urticaceae*) | 7.0% by wt. |
| root of chicory (*Cichorium intybus L, Cichoriaceae*) | 17.7% by wt. |
| leaf of black mulberry (*Morus nigra L, Moraceae*) | 7.4% by wt. |
| flower of yarrow (*Achilleae millefolium L, Asteraceae*) | 3.5% by wt. |
| leaf of bilberry (*Vaccinium myrtillus L, Ericaceae*) | 6.6% by wt. |
| pod of beans (*Phaseolus vulgaris L, Fabaceae*) | 14.4% by wt., and |
| root of valerian (*Valeriana officinalis L, Valerlanaceae*) | 7.8% by wt., |

3. The herbal composition according to claim 1, wherein the composition is processed for oral consumption.

4. The herbal composition according to claim 3, wherein the herbal composition is in the form of a tea, an herbal tincture, or a pill.

5. The herbal composition according to claim 4, wherein the herbal tincture is made by a process comprising the following steps:

a) providing the herbal composition of claim 1, b) covering said herbal composition with 60% ethanol, wherein the step of covering said herbal composition is performed at room temperature to form a mixture, c) resting said mixture in a covered container, wherein the step of resting said mixture in a covered container is performed at about room temperature for a duration of about 28 days, and d) decanting said mixture to obtain the herbal tincture.

6. The herbal composition according to claim 4, wherein the herbal tincture is made by a process comprising the following steps:

a) providing the herbal composition of claim 2, b) covering said herbal composition with 60% ethanol, wherein the step of covering said herbal composition is performed at room temperature to form a mixture, c) resting said mixture in a covered container, wherein the step of resting said mixture in a covered container is performed at about room temperature for a duration of about 28 days, and d) decanting said mixture to obtain the herbal tincture.

7. The herbal composition according to claim 5, wherein the step of covering said herbal composition further comprises providing 7.21 L of 60% ethanol for every 1 kg of said herbal composition.

8. The herbal composition according to claim 6, wherein the step of covering said herbal composition further comprises providing 7.21 L of 60% ethanol for every 1 kg of said herbal composition.

* * * * *